United States Patent [19]

Smith et al.

[11] Patent Number: 5,292,955
[45] Date of Patent: Mar. 8, 1994

[54] AMINE OXIDE COMPLEXES

[75] Inventors: Kim R. Smith; James E. Borland; Joe D. Sauer, all of Baton Rouge, La.

[73] Assignee: Ethyl Corporation, Richmond, Va.

[21] Appl. No.: 902,157

[22] Filed: Jun. 22, 1992

Related U.S. Application Data

[62] Division of Ser. No. 736,251, Jul. 26, 1991, abandoned.

[51] Int. Cl.$^5$ ............................................. C07C 291/04
[52] U.S. Cl. ................................. 564/298; 564/297; 252/547
[58] Field of Search ............................ 564/297, 298

[56] References Cited

U.S. PATENT DOCUMENTS 3,252,979  5/1966  Oswald et al. ........................ 260/268
5,055,233  10/1991  Borland et al. ...................... 252/547

FOREIGN PATENT DOCUMENTS 2365172  7/1975  Fed. Rep. of Germany .
1494109  12/1977  United Kingdom .

OTHER PUBLICATIONS

Oswald et al. J. Am. Chem. Soc. (Mar. 1963) pp. 651–657.

*Primary Examiner*—Allen J. Robinson
*Attorney, Agent, or Firm*—Patricia J. Hogan

[57] ABSTRACT

Novel perhydrates having utility as surfactants and bleaching agents are obtained by reacting an anhydrous amine oxide or an amine oxide monohydrate with hydrogen peroxide in such proportions as to provide a compound corresponding to the formula $RR'R''NO \cdot xH_2O \cdot yH_2O_2$ in which R is a primary alkyl group containing 8-24 carbons; R' is methyl, ethyl, or 2-hydroxyethyl; R'' is independently selected from methyl, ethyl, 2-hydroxyethyl, and primary alkyl groups containing 8-24 carbons; x is 0 or 1; y is 1 or 2; and $x+y$ is $\leq 2$.

9 Claims, No Drawings

AMINE OXIDE COMPLEXES

This application is a division of application Ser. No. 07/736,251, filed Jul. 26, 1991 (now abandoned).

FIELD OF INVENTION

This invention relates to mixed amine oxide perhydrates and processes for preparing them.

BACKGROUND

It is known that many surfactants are useful in cleaning formulations, such as hard surface cleaners and solid or liquid laundry detergents. Among the surfactants which have been found to be particularly useful in these applications are mixed amine oxides, i.e., amine oxides in which the organic groups attached to the amino nitrogen include at least one long-chain group and at least one short-chain group.

The amine oxides employed in the cleaning compositions are most commonly dilute aqueous solutions, since they are ordinarily synthesized as such; but they are sometimes solids obtained by spray-drying, evaporating, or after-treating the dilute solutions.

As taught in copending applications S. N. 07/591,425 (Borland et al.) now U.S. Pat. No. 5,075,501, 07/591,426 (Smith et al.-I) now U.S. Pat. No. 5,130,488, and (Case AM-6292-A) (Smith et al.-II) Ser. No. 07/724,127 (now abandoned), solid amine oxides which have advantages over the dilute solutions and over the solids obtained by previously-known techniques can be produced by preparing the amine oxides completely or partially in dihydrate form and, if desired, then converting the product to an oxide containing a lesser amount of water, e.g., the monohydrate or anhydrous form.

The amine oxides and other surfactants employed in cleaning compositions are frequently employed in conjunction with bleaching agents, such as sodium percarbonate or perborate — materials which are not surface-active themselves. It would be advantageous to develop a material which could serve both as the surfactant and the bleaching agent in such compositions.

Oswald et al., *Journal of the American Chemical Society*, Mar. 1963, pp. 651–657, teach that lower trialkylamine oxides can form unstable hydrogen peroxide adducts which are highly soluble in water and alcohol and only slightly soluble in ether, acetone, and benzene and some of which are crystallizable.

SUMMARY OF INVENTION

The present invention resides in:

(1) novel amine oxide perhydrates corresponding to the formula $RR'R''NO \cdot xH_2O \cdot yH_2O_2$ in which R is a primary alkyl group containing 8–24 carbons; R' is methyl, ethyl, or 2-hydroxyethyl; R'' is independently selected from methyl, ethyl, 2-hydroxyethyl, and primary alkyl groups containing 8–24 carbons; x is 0 or 1; y is 1 or 2; and $x+y$ is $\leq 2$ and (2) processes for preparing the novel perhydrates by reacting an amine oxide or amine oxide monohydrate corresponding to the formula $RR'R''NO \cdot xH_2O$ with y molar proportion(s) of hydrogen peroxide.

DETAILED DESCRIPTION

The amine oxides utilized in preparing the perhydrates of the invention may be any compounds corresponding to the formula $RR'R''NO \cdot xH_2O$ in which R is a primary alkyl group containing 8–24 carbons; R' is methyl, ethyl, or 2-hydroxyethyl; R'' is independently selected from methyl, ethyl, 2-hydroxyethyl, and primary alkyl groups containing 8–24 carbons; and x is 0 or 1. The primary alkyl groups in these compounds may be branched-chain groups; but the preferred compounds are those in which at least most of the primary alkyl groups have a straight chain.

Exemplary of these amine oxides are N-octyldimethylamine oxide, N,N-didecylmethylamine oxide, N-decyl-N-dodecylethylamine oxide, N-dodecyldimethylamine oxide, N-tetradecyldimethylamine oxide, N-tetradecyl-N-ethylmethylamine oxide, N-tetradecyl-N-ethyl-2-hydroxyethylamine oxide, N,N-ditetradecyl-2-hydroxyethylamine oxide, N-hexadecyldimethylamine oxide, N-hexadecyldi-2-hydroxyethylamine oxide, N-octadecyldimethylamine oxide, N,N-dieicosylethylamine oxide, N-docosyl-N-2-hydroxyethylmethylamine oxide, N-tetracosyldimethylamine oxide, the corresponding monohydrates, and mixtures thereof.

When the anhydrous amine oxide or amine oxide monohydrate to be reacted with the hydrogen peroxide is not commercially available, it may be obtained by conventional techniques, e.g., by oxidizing the appropriate tert-amine with hydrogen peroxide in dilute aqueous solution and then recovering an amine oxide in anhydrous or monohydrate form in any suitable manner, e.g., spray-drying or evaporation. However, the desired anhydrous or monohydrate compound can be produced more easily and economically by (1) preparing an amine oxide in which at least some of the molecules are dihydrate molecules, as in Borland et al., Smith et al.-I, or Smith et al.-II, the teachings of all of which are incorporated herein by reference, and (2) removing all or part of the water of hydration by any suitable means.

When an amine oxide is prepared by a process of Borland et al. or Smith et al.-I, (1) the appropriate tert-amine is reacted with concentrated hydrogen peroxide in the presence, during at least the later stages of the reaction, of an organic solvent in which both the amine and amine oxide are soluble at the reaction temperatures but in which the amine oxide is insoluble at a lower temperature, and (2) the water content of the product is adjusted, if necessary to achieve a water/amine oxide mol ratio no higher than about 2.1/1 before the amine oxide is recovered. In this reaction:

(A) the aqueous hydrogen peroxide is employed in at least a stoichiometric amount, and its amount and concentration are preferably such as to make it unnecessary to adjust the water content of the product at the end of the reaction, (B) the organic solvent is used in an amount sufficient to maintain a stirrable reaction mixture and is preferably ethyl acetate, although other substantially inert esters, hydrocarbons halohydrocarbons, and highly polar aprotic solvents are also utilizable, (C) the reaction is conducted by adding the aqueous hydrogen peroxide to the amine, preferably at a controlled rate and preferably in the presence of carbon dioxide and/or a chelating agent (such as diethylenetriaminepentaacetic acid) to improve the reaction rate, at a temperature of 20°–100° C., preferably about 25°–80° C., and (D) the reaction mixture is cooled at the end of the reaction to precipitate the amine oxide.

The process of Smith et al.-II is similar to that of Borland et al. and Smith et al.-I except for utilizing a liquefied gas, preferably liquefied carbon dioxide, as the reaction medium instead of an organic solvent.

When an amine oxide product prepared by a process of Borland et al. or Smith et al.-I or -II has a water/amine oxide mol ratio in the range of about 1.9-2.1/1 at the time that the amine oxide is recovered, the amine oxide is recovered as a dihydrate. When the water/amine oxide mol ratio is lower than about 1.9/1, the recovered amine oxide contains some dihydrate molecules as well as monohydrate and anhydrous molecules.

These dihydrate-containing products have too high a water content to be useful per se in the process of the present invention. However, having lower water contents than amine oxides prepared by conventional techniques, they are more easily and economically converted to monohydrate or anhydrous form. This conversion may be accomplished by any suitable technique, such as those mentioned above. However, it is generally preferred to remove the excess water by azeotropic distillation or by vacuum drying.

The amount of water to be removed from an amine oxide dihydrate-containing product to form a starting material suitable for use in the present invention depends on the particular perhydrate desired. If a perhydrate containing one complexed mol of water and one complexed mol of hydrogen peroxide per mol of amine oxide is desired, water is removed from the dihydrate only until the monohydrate is obtained. However, it is necessary to remove all of the water from the dihydrate (or from a monohydrate) so as to form an anhydrous material when the desired perhydrate is a product containing 1-2 complexed mols of hydrogen peroxide and no complexed water per mol of amine oxide.

In the process of the invention, the anhydrous amine oxide or amine oxide monohydrate is reacted with hydrogen peroxide in such proportions that the sum of the molar proportions of complexed water and hydrogen peroxide in the reaction mixture is not more than two molar proportions per molar proportion of the amine oxide. Thus, the amount of hydrogen peroxide employed may be as much as two mols per mol of amine oxide when the starting amine oxide is anhydrous but should not exceed one molar proportion when the starting amine oxide is a monohydrate. The use of a dihydrate or excess hydrogen peroxide in the reaction leads to gelation on crystallization.

As in the amine oxide dihydrate syntheses of Borland et al. and Smith et al.-I, the process of the invention is advantageously conducted in a solvent from which the product can be easily crystallized by simply lowering the temperature. It is thus preferred to conduct the reaction by (1) mixing the amine oxide starting material with the appropriate amount of a concentrated hydrogen peroxide, i.e., an aqueous hydrogen peroxide having a concentration of 50-80%, preferably 70%, by weight in such a solvent and (2) cooling the solution to crystallize the perhydrate thus formed.

Exemplary of the solvents which may be used in the reaction are those taught by Borland et al. and Smith et al.-I to be utilizable in their amine oxide dihydrate syntheses, e.g.:

(1) saturated and unsaturated aliphatic, cycloaliphatic, and aromatic esters such as methyl formate, ethyl acetate, 1-butenyl formate, 2-isobutenyl propionate, cyclohexyl hexanoate, phenyl acetate, phenethyl propionate, ethyl 2-methyl benzoate, butyl 4-butoxybenzoate, ethylene glycol diacetate, glycerol monoleate, glycerol monostearate, glycerol distearate, glycerol tributyrate, and glucose dibutyrate, (2) liquid aliphatic, cycloaliphatic, and aromatic hydrocarbons such as hexane, isohexane, heptane, 2-ethylhexane, octane, isooctane, cyclohexane, cyclooctane, toluene, and mixtures thereof with up to about 10% (e.g., 2-10%) by weight of a polar cosolvent, such as isopropanol or other alcohol, (3) aromatic halohydrocarbons such as chlorobenzene, dichlorobenzene, bromobenzene, chlorotoluene, and 2,4-dichlorotoluene, and (4) highly polar aprotic solvents such as dimethylformamide, dimethylacetamide, diethylformamide, diethylacetamide, and mixtures thereof.

Since alcohol and acetone are solvents in which the products of the invention are highly soluble and from which crystallization therefore would not be possible, they are not suitable for use in the process.

The preferred solvents for use in the reaction are the alkyl alkanolates, especially those in which the alkyl groups contain 1-5 carbons and the alkanoic moieties contain 2-5 carbons, e.g., the methyl, ethyl, propyl, isopropyl, butyl, sec-butyl, t-butyl, isobutyl, and amyl acetates, propionates, butyrates, and valerates. Ethyl acetate is particularly preferred.

The temperature at which the reaction is conducted may be any temperature at which the reaction will occur without decomposition of the product -- usually a temperature in the range of about 20°-80° C. Since an elevated temperature is not required to achieve reaction, it is generally preferred to accomplish the reaction at room temperature.

When the reactants have been mixed at the desired reaction temperature, the desired perhydrate is formed, and the reaction mixture may then be immediately cooled to a temperature at which the product most easily crystallizes from the product solution or slurry, e.g., a temperature in the range of about 0°-15° C. However, if desired, the product solution or slurry may be diluted with more of the same solvent used in the reaction and/or with a different solvent prior to crystallization. After the product has been crystallized, it may be recrystallized one or more times to increase its purity.

The crystallized product may be recovered by conventional means, e.g., filtration or centrifugation, and it is usually also desirable to dry it, e.g., by vacuum drying.

The products of the invention are perhydrates which, whether they have two hydrogen peroxide molecules, one hydrogen peroxide molecule, or one hydrogen peroxide molecule and one water molecule complexed with the amine oxide molecule, are surprising heat stable and thus capable of functioning both as bleaching agents and surfactants in applications such as laundry detergents, "color-safe" oxygen bleaches, and hard surface cleaners.

The following examples are given to illustrate the invention and are not intended as a limitation thereof.

EXAMPLE I

Dissolve 100g of N-tetradecyldimethylamine oxide monohydrate in 200 mL of ethyl acetate. Add 17.7g of 70% hydrogen peroxide and then cool the solution to 5° C. to crystallize a product having the formula $C_{14}H_{29}(CH_3)_2NO \cdot H_2O \cdot H_2O_2$. Test the product for stability of the peroxide by heating it from 25° C. to 200° C. Differential scanning calorimetry (DSC) shows no exotherm — evidence of the heat stability of the peroxide.

EXAMPLE II

Repeat Example I except for replacing the N-tetradecyldimethylamine oxide monohydrate with an equimolar amount of anhydrous N-tetradecyldimethylamine oxide. Similar results are observed except that the product is a complex having the formula $C_{14}H_{29}(CH_3)_2NO \cdot H_2O_2$.

EXAMPLE III

Repeat Example II except for doubling the amount of hydrogen peroxide added. Similar results are observed except that the product is a complex having the formula $C_{14}H_{29}(CH_3)_2NO \cdot 2H_2O_2$.

COMPARATIVE EXAMPLE A

Repeat Example I except for adding 35g of the 70% hydrogen peroxide solution. Attempts to crystallize the product give gel rather than a solid product.

COMPARATIVE EXAMPLE B

Repeat Example I except for replacing the monohydrate with N-tetradecyldimethylamine oxide dihydrate and adding 16.6g of 70% hydrogen peroxide. Attempts to crystallize the product give gel instead of a solid product.

What is claimed is:

1. A process which comprises (1) reacting one molar proportion of an amine oxide corresponding to the formula:

$$RR'R''NO \cdot xH_2O$$

with y molar proportions of an aqueous hydrogen peroxide having a concentration of 50–80% by weight in an organic solvent to form a solution of perhydrate corresponding to the formula:

$$RR'R''NO \cdot xH_2O \cdot yH_2O_2$$

and (2) cooling the solution to crystallize the perhydrate; R in the above formulas being a primary alkyl group containing 8–24 carbons; R' being methyl, ethyl, or 2-hydroxyethyl; R'' being independently selected from methyl, ethyl, 2-hydroxyethyl, and primary alkyl groups containing 8–24 carbons; x being 0 or 1; y being 1 or 2; and the sum of x and y being 2.

2. The process of claim 1 wherein both x and y are 1.

3. The process of claim 2 wherein R' is methyl.

4. The process of claim 3 wherein R is tetradecyl and R'' is methyl.

5. The process of claim 3 wherein R and R'' are tetradecyl.

6. The process of claim 1 wherein x is 0 and y is 2.

7. The process of claim 6 wherein R' is methyl.

8. The process of claim 7 wherein R is tetradecyl and R'' is methyl.

9. The process of claim 7 wherein R and R'' are tetradecyl.

* * * * *